US00RE46151E

(19) United States
(12) Reissued Patent
Gralla et al.

(10) Patent Number: US RE46,151 E
(45) Date of Reissued Patent: Sep. 20, 2016

(54) METHOD FOR THE PRODUCTION OF 4,4'-[1-(TRIFLUOROMETHYL)ALKYLIDENE]-BIS-(2,6-DIPHENYLPHENOLS)

(71) Applicant: BASF SE, Ludwigshafen OT (DE)

(72) Inventors: Gabriele Gralla, Mannheim (DE); Gunnar Heydrich, Limburgerhof (DE); Klaus Ebel, Lampertheim (DE); Wolfgang Krause, Bruehl-Rohrhof (DE)

(73) Assignee: BASF SE, Ludwigshafen (DE)

(21) Appl. No.: 14/321,865

(22) Filed: Jul. 2, 2014

Related U.S. Patent Documents

Reissue of:
(64) Patent No.: 8,212,084
Issued: Jul. 3, 2012
Appl. No.: 12/808,865
PCT Filed: Dec. 17, 2008
PCT No.: PCT/EP2008/067686
§ 371 (c)(1),
(2) Date: Jun. 17, 2010
PCT Pub. No.: WO2009/077549
PCT Pub. Date: Jun. 25, 2009

(30) Foreign Application Priority Data

Dec. 17, 2007 (EP) ..... 07123368

(51) Int. Cl.

| | |
|---|---|
| ***C07C 39/16*** | (2006.01) |
| ***C07C 39/12*** | (2006.01) |
| ***C07C 45/74*** | (2006.01) |
| ***C07C 37/07*** | (2006.01) |
| ***C07C 37/20*** | (2006.01) |
| ***C07C 37/62*** | (2006.01) |

(52) U.S. Cl.
CPC ..... *C07C 45/74* (2013.01); *C07C 37/07* (2013.01); *C07C 37/20* (2013.01); *C07C 37/62* (2013.01)

(58) Field of Classification Search
CPC ..... C07C 37/07; C07C 37/20; C07C 37/62; C07C 45/74; C07C 49/613; C07C 49/653; C07C 39/15; C07C 39/367
USPC ..... 568/718, 747
See application file for complete search history.

(56) References Cited

U.S. PATENT DOCUMENTS

| | | | | |
|---|---|---|---|---|
| 3,679,766 | A | 7/1972 | Kippax et al. | |
| 3,739,035 | A | 6/1973 | Webb et al. | |
| 4,080,390 | A * | 3/1978 | Imamura | 568/747 |
| 7,608,742 | B2 | 10/2009 | Friedrich et al. | |
| 2010/0010253 | A1 | 1/2010 | Heydrich et al. | |
| 2010/0016642 | A1 | 1/2010 | Heydrich et al. | |
| 2010/0206712 | A1 | 8/2010 | Heydrich et al. | |
| 2010/0249467 | A1 | 9/2010 | Heydrich et al. | |

FOREIGN PATENT DOCUMENTS

| | | | |
|---|---|---|---|
| DE | 1643402 | A1 | 5/1970 |
| DE | 1643403 | A1 | 4/1971 |
| DE | 2211721 | A1 | 9/1972 |
| GB | 1207524 | A | 10/1970 |
| JP | S52-3041 | | 1/1977 |
| JP | S52-17450 | | 2/1977 |
| JP | S52-27156 | | 7/1977 |
| WO | WO-2006/092433 | A1 | 9/2006 |

OTHER PUBLICATIONS

Bibo et al., "Analysis of 2,6-Substituted Cyclohexanones and Phenols by Gas-Chromatography Combined with Thin-Layer Chromatography," *Z, Anal Chem.*. vol. 236, pp. 208-215 (1967).
Database CAPLUS on STN, Acc. No. 1982:405891, Dana et al., Synthesis (1982), 2, p. 164-165 (abstract).

* cited by examiner

*Primary Examiner* — Evelyn Huang
(74) *Attorney, Agent, or Firm* — Drinker Biddle & Reath LLP

(57) ABSTRACT

The present invention relates to a process for preparing 4,4'-[1-(trifluoromethyl)alkylidene]bis(2,6-diphenylphenols), in particular for preparing 4,4'-[1-(trifluoromethyl)ethylidene]bis(2,6-diphenylphenol), which comprises the self-condensation of cyclohexanone in the presence of a basic catalyst to form tricyclic condensation products, dehydrogenation of the resulting tricyclic condensation products in the presence of a supported transition metal catalyst in the condensed phase to form 2,6-diphenylphenol and reaction of the 2,6-diphenylphenol with a trifluoromethyl ketone. The invention further provides an improved process for preparing 2,6-diphenylphenol by aldol self-condensation of cyclohexanone.

21 Claims, No Drawings

METHOD FOR THE PRODUCTION OF 4,4'-[1-(TRIFLUOROMETHYL)ALKYLIDENE]-BIS-(2,6-DIPHENYLPHENOLS)

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application is a national stage application (under 35 U.S.C. §371) of PCT/EP2008/067686, filed Dec. 17, 2008, which claims benefit of European Application No. 07123368.8, filed Dec. 17, 2007.

The present invention relates to a process for preparing 4,4'-[1-(trifluoromethyl)alkylidene]bis(2,6-diphenylphenols), in particular for preparing 4,4'-[1-(trifluoromethyl)ethylidene]bis(2,6-diphenylphenol), which comprises the self-condensation of cyclohexanone in the presence of a basic catalyst to form tricyclic condensation products, dehydrogenation of the resulting tricyclic condensation products in the presence of a supported transition metal catalyst in the condensed phase to form 2,6-diphenylphenol and reaction of the 2,6-diphenylphenol with a trifluoromethyl ketone. The invention further provides an improved process for preparing 2,6-diphenylphenol by aldol self-condensation of cyclohexanone and subsequent dehydrogenation.

4,4'-[1-(Trifluoromethyl)ethylidene]bis(2,6-diphenylphenol) and 4,4'-[1,1-bis(trifluoromethyl)methylidene]bis(2,6-diphenylphenol) are known from U.S. Pat. No. 3,739,035 and are described as valuable starting materials for preparing polycarbonates or polyesters. They are prepared by reacting 2,6-diphenylphenol with in each case large excesses of gaseous hexafluoroacetone or 1,1,1-trifluoroacetone in methanesulfonic acid.

The compounds mentioned are also important starting materials for preparing bis(diarylphenoxy)aluminum compounds as are described in WO 2006/092433.

DE 1 643 402 relates to a process for preparing 2,6-diphenylphenol by self-condensation of cyclohexanone to form tricyclic condensation products and subsequent dehydrogenation of these. Here, the self-condensation of cyclohexanone is carried out under solvent-free conditions at temperatures of up to 200° C. in the presence of a strong base, preferably aqueous solutions of sodium hydroxide or potassium hydroxide, as catalyst. The dehydrogenation of the tricyclic condensation products obtained in admixture with bicyclic condensation products which is to be carried out in the second step is carried out in the presence of a dehydrogenation catalyst at a temperature of up to 350° C., preferably from 300 to 350° C. Suitable dehydrogenation catalysts described are supported platinum, palladium, nickel, ruthenium and rhodium catalysts.

DE 1 643 403 discloses a process for crystallizing 2,6-diphenylphenol from a mixture comprising 2,6-diphenylphenol together with at least one further phenol which has an aliphatic 6-membered ring instead of a phenyl ring in the 2 or 6 position. For this purpose, the mixtures are dissolved in a mixture of from 75 to 99% by weight of an aliphatic solvent with from 1 to 25% by weight of an aromatic solvent and the temperature of the solution is reduced to a point below the crystallization temperature of 2,6-diphenylphenol.

DE 2 211 721 relates to a process for preparing orthophenylphenol, wherein the product of the bimolecular dehydration condensation of cyclohexanone is introduced into a bed of a catalyst supported on an inactive support and the condensate is subjected to dehydrogenation at from 230 to 520° C. in the presence of an inert gas. The document also discloses catalysts which are suitable for carrying out the process and comprise one or more of the elements palladium, platinum, iridium and rhodium and may further comprise an alkali.

Proceeding from this prior art, it was an object of the present invention to provide a process which makes it possible to prepare 4,4'-[1-(trifluoromethyl)alkylidene]bis(2,6-diphenylphenols) and 2,6-diphenylphenol in a particularly economical manner, i.e. with a very high yield of the desired compounds and with very little formation of undesirable by-products which may, if appropriate, have to be separated off in a complicated fashion and be disposed of or recirculated, and in a manner which is very advantageous from a process engineering point of view.

The object was achieved according to the invention by provision of a process for preparing 4,4'-[1-(trifluoromethyl)alkylidene]bis(2,6-diphenylphenols) of the formula (I)

(I)

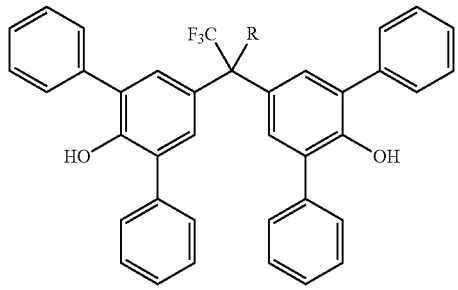

where the radical

R is unbranched or branched $C_1$-$C_6$-alkyl or $C_1$-$C_6$-perfluoroalkyl, which comprises the process steps a) reaction of cyclohexanone in the presence of a basic catalyst to form a reaction mixture comprising the tricyclic condensation products of the formula (IIa), (IIb) and/or (IIc)

(IIa)

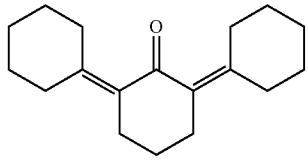

(IIb)

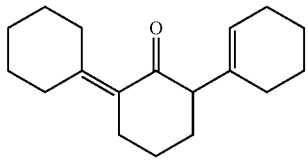

(IIc)

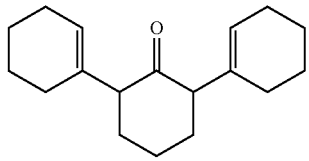

and water, b) separation of a mixture of the tricyclic condensation products comprising the compounds of the formulae (IIa), (IIb) and/or (IIc) from the reaction mixture formed in step a), c) dehydrogenation of the tricyclic condensation products comprising the compounds of the formulae (IIa), (IIb) and/or (IIc) obtained in step b) in the presence of a supported transition metal catalyst in the condensed phase to form a reaction mixture comprising 2,6-diphenylphenol of the formula (III), (III)

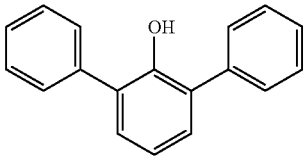

d) separation of 2,6-diphenylphenol of the formula (III) from the reaction mixture formed in step c) and e) reaction of the 2,6-diphenylphenol of the formula (III) obtained in step d) with a trifluoromethyl ketone of the formula (IV)

(IV)

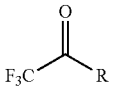

where the radical R is as defined for formula (I), in the presence of a strong organic acid to form the 4,4'-[1-(trifluoromethyl)alkylidene]bis(2,6-diphenylphenol) of the formula (I).

The process of the invention is suitable for preparing 4,4'-[1-(trifluoromethyl)alkylidene]bis(2,6-diphenylphenols) of the formula (I)

(I)

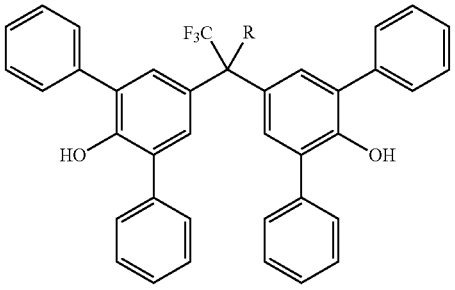

where the radical R is unbranched or branched $C_1$-$C_6$-alkyl or $C_1$-$C_6$-perfluoroalkyl. Here, the term branched or unbranched $C_1$-$C_6$-alkyl refers to branched or unbranched alkyl radicals having from 1 to 6 carbon atoms, for example methyl, ethyl, propyl, isopropyl, butyl, sec-butyl, tert-butyl, pentyl or hexyl. Preferred $C_1$-$C_6$-alkyl radicals are methyl, ethyl, isopropyl, particularly preferably methyl. The term branched or unbranched $C_1$-$C_6$-perfluoroalkyl refers to branched or unbranched perfluoroalkyl radicals, i.e. alkyl radicals in which all hydrogen atoms have been replaced by fluorine atoms, having from 1 to 6 carbon atoms, for example trifluoromethyl, pentafluoroethyl, heptafluoropropyl, heptafluoroisopropyl, nonafluorobutyl. Preferred $C_1$-$C_6$-perfluoroalkyl radicals are trifluoromethyl, pentafluoroethyl, heptafluoroisopropyl, particularly preferably trifluoromethyl. Possible particularly preferred process products are accordingly 4,4'-[1-(trifluoromethyl)ethylidene]bis(2,6-diphenylphenol) of the formula (Ia)

(Ia)

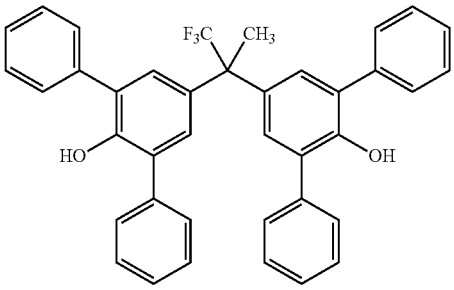

and 4,4'-[1,1-(bistrifluoromethyl)methylidene]bis(2,6-diphenylphenol) of the formula (Ib)

(Ib)

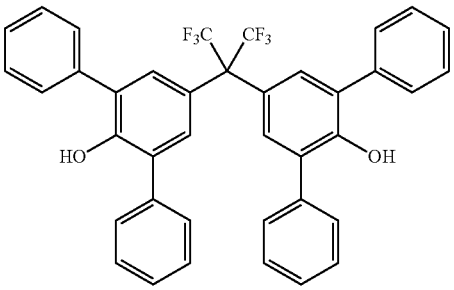

A process product which is very particularly preferred according to the invention is 4,4'-[1-(trifluoromethyl)ethylidene]bis(2,6-diphenylphenol) of the formula (Ia).

The process of the invention comprises the process steps a) to e). In process step a) of the process of the invention, a reaction of cyclohexanone in the presence of a basic catalyst is carried out to form a reaction mixture comprising the tricyclic condensation products of the formula (IIa), (IIb) and/or (IIc)

(IIa)

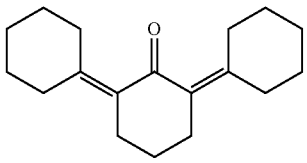

(IIb)

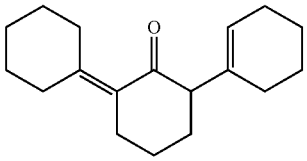

-continued (IIc)

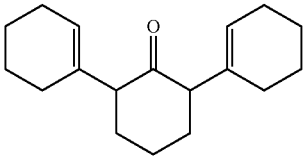

and water. Accordingly, cyclohexanone serves as starting material for carrying out the process of the invention. This can be used in commercial purity, i.e. without particular purity requirements, production process or nature, usually in a purity of about 95% by weight or above, preferably 99% by weight or above.

The reaction of cyclohexanone according to step a) of the process of the invention is an intermolecular self-condensation of 3 molecules of cyclohexanone in an aldol condensation (aldol addition with subsequent elimination of water), as is known per se to those skilled in the art. This forms product mixtures of tricyclic cyclohexanones which comprise the compounds of the formulae (IIa), (IIb) and/or (IIc) depicted above. The mixtures mentioned can comprise one, two or all three of the compounds (IIa), (IIb) and (IIc) mentioned and may additionally comprise further isomers of the compounds mentioned, for example those in which an ethylenic double bond is localized in the cyclohexanone ring of the molecule. It is usual for all three tricyclic ketones of the formulae (IIa), (IIb) and (IIc) to be present in the product mixtures mentioned.

Bicyclic cyclohexanones, especially those of the formulae (Va) and/or (Vb)

(Va)

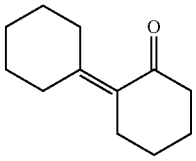

(Vb)

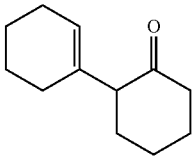

are generally also formed as undesirable by-products of the self-condensation of cyclohexanone to be carried out in step a) of the process of the invention. However, these can, as described below under step b) of the process of the invention, be separated off from the tricyclic reaction products of the formulae (IIa), (IIb) and/or (IIc), preferably by distillation, and, if desired, be recirculated to the reaction in process step a).

The reaction in process step a) is carried out in the presence of a basic catalyst, preferably in the presence of an inorganic, especially strongly basic, catalyst. As basic or strongly basic, in particular inorganic, catalysts or bases, mention may be made of those which are able to convert cyclohexanone at least partly into the corresponding enolate anion by deprotonation. The reaction in process step a) is preferably carried out in the presence of a strong base, particularly preferably a base which has a pKb of less than 4. As preferred strong bases for this purpose, mention may be made of the hydroxides, alkoxides, hydrides, amides or carbonates of alkali metals or alkaline earth metals, for example lithium, sodium, potassium, calcium and barium hydroxide, sodium ethoxide, sodium methoxide, potassium tert-butoxide, sodium and potassium hydride, lithium diisopropylamide and also lithium, sodium, potassium, calcium and barium carbonate. Particularly preferred strong bases are the hydroxides and carbonates of the alkali metals or alkaline earth metals, very particularly preferably the hydroxides of the alkali metals. The compounds mentioned can be used in pure form or in the form of mixtures with one another or in the form of mixtures with other bases. They can be used in solid or dissolved form, preferably in the form of aqueous solutions.

The amount of basic catalyst to be used in process step a) is not critical and can be varied within a wide range. However, taking into account the economic aspect, it is advantageous to use the catalyst in the smallest possible amount, preferably in an amount of up to 20 mol %, particularly preferably up to 10 mol % and very particularly preferably up to 5 mol %, in each case based on the base equivalents and the amount of cyclohexanone used.

In process step a) of the process of the invention, preference is given to using an aqueous solution of an alkali metal hydroxide or alkaline earth metal hydroxide, particularly preferably an aqueous solution of sodium hydroxide, as basic catalyst. If the base selected is used in the form of a solution, preferably in the form of an aqueous solution, the preferred concentration range of these solutions is from about 5 to about 50% by weight (based on the finished solution), particularly preferably from about 25 to about 50% by weight.

The self-condensation of cyclohexanone to be carried out in process step a) can be carried out in a wide temperature range, usually at temperatures of from about 70° C. to about 200° C. A preferred temperature range for carrying out process step a) of the process of the invention is the range from 90 to 180° C.

During the course of the self-condensation of the cyclohexanone used, i.e. as conversion progresses, the dimeric, bicyclic condensation products of the formulae (Va) and (Vb) are firstly formed as primary condensation products from the reaction of two molecules of cyclohexanone. These have a boiling point higher than that of cyclohexanone itself and have to react with a further molecule of cyclohexanone to form the desired tricyclic condensation products of the formulae (IIa), (IIb) and/or (IIc).

In an embodiment of the process of the invention which is particularly preferred according to the invention, the reaction according to process step a) is carried out in the presence of a solvent (other than cyclohexanone) or solvent mixture which forms an azeotrope with water. Preferred "solvents which form an azeotrope with water" are solvents, preferably organic solvents, which are inert under the reaction conditions and have a boiling point at atmospheric pressure of from about 100° C. to about 200° C., preferably in the range from 100° C. to 150° C., particularly preferably in the range from 110° C. to 140° C. and very particularly preferably in the range from 130° C. to 140° C., and are different from cyclohexanone. Particular preference is given to those organic solvents which form an azeotrope with water which has a boiling point lower than that of cyclohexanone, i.e. less than 155° C., and a boiling point lower than that of the respective solvent itself (low-boiling azeotrope). Very particular preference is given to those solvents or solvent mixtures whose azeotropic boiling point is below the azeotropic boiling point of cyclohexanone of 95° C. To ensure a satisfactory reaction rate, it is advantageous for the azeotropic boiling point of the solvent or solvent mixture selected to be as high as possible, preferably 70° C. or above, particularly preferably 80° C. or above. In process step a) of the process of the invention, solvents which can particularly preferably be used according to the invention accordingly have an azeotropic boiling point in the range from 70° C. to 95° C., preferably from 80° C. to 95° C., particularly preferably up to <95° C., for example toluene, xylene and ethylbenzene or mixtures thereof, preferably xylene. The abovementioned "solvent which forms an azeotrope with water" can therefore also be referred to as an entrainer.

The solvents mentioned can be used as such or in the form of mixtures of two or more different solvents. Preference is given to using only one solvent, preferably a solvent which forms an azeotrope as described above with water, in process step a) of the process of the invention.

In another preferred embodiment, the process of the invention is carried out so that the water formed in process step a) by aldol self-condensation of cyclohexanone is separated from the reaction mixture by distillation in the form of an azeotrope with the solvent used during the reaction. The removal of the water of reaction formed in the aldol self-condensation of cyclohexanone and any water added in the form of an aqueous solution of the basic catalyst can be carried out by azeotropic distillation methods known per se to those skilled in the art using apparatuses which are likewise known for the separation or removal of water from a reaction mixture, for example a water separator. The water can be separated off completely or largely completely or only partly. However, preference is given to separating off the stoichiometrically expected amount of water to be formed (and also any amount of water added with the catalyst) as completely as possible in order to aid the desired formation of the above-mentioned tricyclic reaction products.

The amount of solvent which forms an azeotrope with water to be used in this preferred embodiment can be selected within a wide range and can be dependent on various factors, in particular on the choice of the specific solvent or solvent mixture used and on the process or apparatus used for separating off or removing the water. The selected solvent is usually, taking account of economic factors, used in an amount of from 5 to 100% by weight, preferably from 10 to 60% by weight and particularly preferably from 15 to 40% by weight, of the amount of cyclohexanone used.

This gives a reaction mixture which comprises, apart from the basic catalyst used, essentially the desired tricyclic ketones of the formulae (IIa), (IIb) and/or (IIc) together with bicyclic condensation products of the formula (Va) and/or (Vb) and unreacted cyclohexanone. The reaction mixture obtained in this way can be processed further in this form or firstly be worked up, for example by extractive processes with which those skilled in the art will be familiar. It is advantageous firstly to carry out a neutralization of the basic catalyst by treatment with an acid.

In process step b) of the process of the invention, the tricyclic condensation products comprising the compounds of the formulae (IIa), (IIb) and/or (IIc) are separated off from the optionally worked-up and largely neutralized reaction mixture formed in this way in process step a). The separation can be effected by methods which appear suitable to those skilled in the art, for example by chromatography or distillation. The separation of the tricyclic reaction products of the formulae IIa, IIb and/or IIc from the reaction mixture obtained in process step a), if appropriate after neutralization and work-up by extraction, in process step b) is preferably carried out in the form of a distillation.

The isolation of the tricyclic condensation products by distillation can be carried out batchwise, semicontinuously or fully continuously. Preference is given to carrying out a batch or semicontinuous distillation, particularly preferably a batch distillation. The design of the distillation column to be used does not have to meet any particular requirements. It can be advantageous to use packed columns, e.g. columns packed with suitable mesh packing, sheetmetal packing or disordered beds of packing elements. The distillation is advantageously carried out under reduced pressure, preferably at a pressure at the bottom of from about 1 to about 100 mbar, particularly preferably from about 5 to about 30 mbar abs., and a pressure at the top of from about 1 to about 100 mbar abs., particularly preferably from about 5 to about 20 mbar abs. Accordingly, the temperature at the bottom is advantageously from about 200 to about 250° C., preferably from about 210 to about 230° C., and the temperature at the top is from about 190 to about 220° C., preferably from about 200 to about 210° C. The tricyclic ketones of the formulae (IIa), (IIb) and/or (IIc) are obtained as high-boiling bottom product from which the lower-boiling components, in particular the bicyclic condensation products of the formulae (Va) and/or (Vb), are distilled off as overhead product. These can, if desired, be recirculated as starting material to the aldol self-condensation of cyclohexanone in process step a) of the process of the invention.

In process step c) of the process of the invention, a dehydrogenation of the tricyclic condensation products comprising the compounds of the formula (IIa), (IIb) and/or (IIc) obtained according to process step b) is carried out in the presence of a supported transition metal catalyst in the condensed phase to form a reaction mixture comprising 2,6-diphenylphenol of the formula (III)

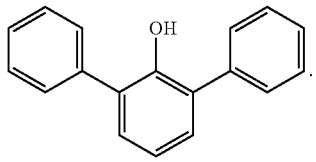

(III)

The dehydrogenation step in process step c) of the process of the invention is carried out in the condensed, i.e. liquid, phase. Here, the mixture comprising the tricyclic ketones of the formulae (IIa), (IIb) and/or (IIc) to be reacted and the 2,6-diphenylphenol of the formula (III) obtained as dehydrogenation product and also any partially dehydrogenated compounds obtained, for example 2-cyclohexyl-6-phenylphenol, are present largely, i.e. predominantly, in liquid form. The dehydrogenation is usually carried out at elevated temperature, preferably at temperatures in the range from about 200° C. to about 300° C., i.e. at temperatures below the boiling point of the tricyclic starting materials mentioned or products of the dehydrogenation. The dehydrogenation is preferably carried out at a temperature in the range from 240 to 300° C., particularly preferably in the range from 250 to 300° C.

Furthermore, the dehydrogenation in process step c) is carried out in the presence of a supported transition metal catalyst. Suitable supported transition metal catalysts are in principle all those which are known to those skilled in the art as catalysts for such dehydrogenation reactions to form aromatic systems, for example those comprising one or more of the transition metals palladium, platinum, nickel, ruthenium, rhodium on a suitable support. The dehydrogenation in process step c) is preferably carried out in the presence of a catalyst comprising palladium (Pd) and/or platinum (Pt) on a support. The catalysts which are preferably to be used in process step c) can comprise the transition metals palladium and platinum either individually or in the form of a mixture with one another, if appropriate together with further metals. Preference is given to using catalysts which comprise palladium as catalytically active metal. The metals mentioned are used in supported form, i.e. in a form in which they have been applied to materials which are known per se to those skilled in the art as support materials. As suitable support materials, mention may be made by way of example of: silica gel ($SiO_2$), aluminum oxide ($Al_2O_3$), carbon, activated carbon, zirconium oxide ($ZrO_2$), titanium dioxide ($TiO_2$). In a preferred embodiment, the dehydrogenation in process step c) of the process of the invention is carried out in the presence of a Pd catalyst supported on $Al_2O_3$ or on a carbon support such as activated carbon. Here, the $Al_2O_3$ can be used in the form of $\gamma$-$Al_2O_3$ (gamma-$Al_2O_3$) or in the form of $\delta$-$Al_2O_3$ (delta-$Al_2O_3$) or in the form of $\theta$-$Al_2O_3$ (theta-$Al_2O_3$) or in the form of $\delta/\theta$-$Al_2O_3$ (delta/theta-$Al_2O_3$) or in the form of $\alpha$-$Al_2O_3$ (alpha-$Al_2O_3$), as described, for example, in Hollemann Wiberg, Lehrbuch der Anorganischen Chemie, 102nd edition, de Gruyter, 2007, page 1161. Preference is given to using $\gamma$-$Al_2O_3$ (gamma-$Al_2O_3$) as support. A supported catalyst which is particularly preferred for the purposes of the present invention is therefore Pd on $\gamma$-$Al_2O_3$ (gamma-$Al_2O_3$).

The catalytically active metals, preferably palladium and/or platinum, are usually present in the supported catalyst in a proportion by weight of from about 0.1 to about 20% by weight, preferably from about 0.1 to 10% by weight (in each case based on the finished catalyst). They are usually, depending on the type of catalyst used, used in an amount of from 1 to 40% by weight, preferably from 1 to 35% by weight, based on the weight of the mixture of tricyclic ketones to be dehydrogenated.

The supported transition metal catalyst to be used according to the invention can be used in a wide variety of forms known to those skilled in the art, for example in the form of spheres, extrudates or as powder.

In a further preferred embodiment, the dehydrogenation in process step c) can be carried out in the presence of hydroxides or carbonates of alkali metals or alkaline earth metals, for example in the presence of lithium, sodium, potassium, calcium or barium hydroxide and/or lithium, sodium, potassium, calcium or barium carbonate, in addition to the supported transition metal catalyst used. The basic compounds mentioned can, depending on the type of compound or compounds used, be used in an amount of usually from 3 to 20% by weight based on the supported catalyst used. As an alternative, it is also possible to use supports or supported catalysts which have been treated with the above-mentioned alkali metal or alkaline earth metal hydroxides or carbonates.

The dehydrogenation in process step c) generally proceeds quickly and at the reaction temperatures mentioned is usually substantially complete after about 24 h, often after about 12 h or less. The dehydrogenation gives a reaction mixture which comprises the fully dehydrogenated compound 2,6-diphenylphenol of the formula (III), generally together with tricyclic ketones which have not been dehydrogenated or been only partially dehydrogenated.

The heterogeneous dehydrogenation catalysts described above can be separated off by methods with which those skilled in the art are familiar, for example by filtration or centrifugation, preferably by filtration. When the above-described supported transition metal catalysts are used, in particular when the abovementioned catalyst comprising palladium (Pd) and/or platinum (Pt) on a support is used, it has been found that the catalysts separated off after the reaction in process step c) generally still have a high activity. They can therefore advantageously be reused, preferably in further reactions as per process step c). In a preferred embodiment of the process of the invention, the catalyst used in process step c) is therefore separated off from the reaction mixture after the reaction has been carried out and is reused in one or more further reactions as per process step c).

The catalyst which has been recovered in each case can in principle be used for as long and as often as it still retains the desired activity. This generally depends on the catalyst selected in each case, on the starting materials selected and on the reaction conditions. When a catalyst comprising palladium (Pd) and/or platinum (Pt), especially palladium (Pd) on a support is used, this can usually be recirculated, i.e. reused, up to ten or more times, but at least up to five times or up to four times, without appreciable decreases in activity or selectivity in the dehydrogenation reaction occurring.

The above-described addition of hydroxides or carbonates of alkali metals or alkaline earth metals in process step c), which is preferred according to the invention, can also have an advantageous effect on the activity, operating life or reusability of the supported transition metal catalyst used in each case. The addition of alkali metal or alkaline earth metal carbonates, preferably sodium and/or potassium carbonate and very particularly preferably potassium carbonate ($K_2CO_3$), in particular, can lead to an increase in activity and thus to improved reusability of the particular supported catalyst used. This effect is particularly pronounced in reactions using supported palladium catalysts, especially in reactions using the particularly preferred Pd on $\gamma$-$Al_2O_3$ (gamma-$Al_2O_3$) as catalyst. In a particularly preferred embodiment, step c) of the process of the invention is accordingly carried out in the presence of Pd on $\gamma$-$Al_2O_3$ (gamma-$Al_2O_3$) as supported transition metal catalyst and in the presence of an alkali metal carbonate, preferably in the presence of potassium carbonate.

In process step d) of the process of the invention, a separation of 2,6-diphenylphenol of the formula (III) from the reaction mixture formed in process step c) is carried out. The separation according to process step d) can in principle be carried out by means of customary methods for effecting separation of materials, for example distillation, chromatography or crystallization. It has been found to be advantageous to separate 2,6-diphenylphenol from the undesirable undehydrogenated or only partially dehydrogenated tricyclic ketones by crystallization. Solvents which have been found to be suitable for this purpose are lower hydrocarbons having up to 8 carbon atoms, for example pentane, hexane, cyclohexane, heptane, octane, toluene, xylene, if appropriate in admixture with lower aliphatic alcohols having from 1 to 4 carbon atoms, e.g. methanol, ethanol, propanol, isopropanol or butanol, or with ketones, ethers or esters having up to 5 carbon atoms, for example acetone, tert-butyl methyl ether or ethyl acetate. It has been found to be particularly advantageous to carry out the isolation of 2,6-diphenylphenol according to process step d) in the form of a crystallization from heptane or a heptane-comprising solvent mixture. Pure heptane or a mixture of heptane and isopropanol in a volume ratio of from about 20:1 to about 30:1 has been found to be very particularly useful as solvent or solvent combination. The term heptane encompasses both n-heptane and also isomers thereof, for example 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethylbutane or mixtures thereof.

The 2,6 diphenylphenol of the formula (III) obtained by the above-described crystallization can subsequently be separated off from the mother liquor in the customary manner, preferably by filtration or centrifugation.

In this way, 2,6-diphenylphenol of the formula (III) can be obtained in pure form, i.e. in a purity of at least 98% by weight, often at least 99% by weight. This material is low in undesirable undehydrogenated or only partially dehydrogenated tricyclic ketones which would be separated off only with difficulty in further process steps or reactions and would lead to undesirable product mixtures and secondary reactions.

In process step e) of the process of the invention, the 2,6-diphenylphenol of the formula (III) obtained in process step d) is reacted with a trifluoromethyl ketone of the formula (IV)

(IV)

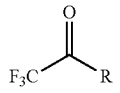

where the radical R is as defined for formula (I), in the presence of a strong organic acid to form the 4,4-[1-(trifluoromethyl)alkylidene]bis(2,6-diphenylphenol) of the formula (I).

Depending on the desired target compound, the 2,6-diphenylphenol prepared according to process steps a) to d) is reacted in process step e) with a trifluoromethyl ketone of the formula (IV), where the radical R can be $C_1$-$C_6$-alkyl or $C_1$-$C_6$-perfluoroalkyl as described above for the compounds of the formula (I). To prepare the process products of the formulae (Ia) and (Ib) which are particularly preferred according to the invention, the 2,6-diphenylphenol obtained in process step d) is accordingly reacted either with 1,1,1-trifluoroacetone of the formula (IVa)

(IVa)

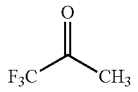

or with hexafluoroacetone of the formula (IVb)

(IVb)

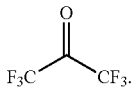

Both reagents can be used in commercial form without any particular requirements in terms of purity or production process. Hexafluoroacetone of the formula (IVb) is preferably passed in gaseous form into the reaction mixture.

The chosen trifluoromethyl ketone is advantageously used according to the stoichiometry of the reaction, preferably in a slight excess. The compounds 2,6-diphenylphenol and the trifluoromethyl ketone of the formula (IV) selected are usually used in a molar ratio of from about 1:1 to about 2:1, preferably from about 2.0:1.2 to about 2.0:1.1.

The reaction in process step e) is carried out in the presence of a strong organic acid, preferably an organic acid having a pKa of up to 2, particularly preferably a pKa in the range from −1 to 2, very particularly preferably a pKa in the range from 1 to 2. As preferred organic acids which can be used in process step e), mention may be made of sulfonic acids, especially alkylsulfonic or phenylsulfonic acids. Preferred sulfonic acids are, for example: methanesulfonic acid, trifluoromethanesulfonic acid, benzenesulfonic acid, para-toluene-sulfonic acid, particularly preferably methanesulfonic acid or trifluoromethanesulfonic acid and very particularly preferably methanesulfonic acid.

The strong organic acid selected, preferably methanesulfonic acid or trifluoromethanesulfonic acid, particularly preferably methanesulfonic acid, is used in undiluted form (100% strength) in a preferred embodiment. The acid is usually used in a significant excess over the amount of 2,6-diphenylphenol to be reacted. In general, with a view to economic aspects, a weight ratio of the acid selected to 2,6-diphenylphenol of from about 10:1 to about 30:1, preferably from about 10:1 to about 20:1, is selected.

To carry out the reaction according to process step e), the selected reagents can be brought into contact with one another in any order, usually at temperatures in the range from 0 to 100° C. The reaction according to process step e) is preferably carried out at a temperature in the range from 10 to 60° C., particularly preferably in the range from 20 to 50° C. The reaction is then usually largely complete after reaction times of from 10 to 24 hours.

The target compound of the formula (I), which is generally obtained in solid form, can be isolated from the resulting reaction mixture by conventional separation methods, preferably by filtration or preferably by extraction, preferably by extraction with toluene, xylene or ethylbenzene or mixtures thereof. In a preferred embodiment, the process of the invention is carried out with the 4,4'-[1-(trifluoromethyl)alkylidene]bis(2,6-diphenylphenols) of the formula (I) formed in process step e) being separated off from the resulting reaction mixture by extraction. An extractant which is particularly preferred in this embodiment is toluene. In this way, the organic acid used, preferably the methanesulfonic acid or trifluoromethanesulfonic acid used, can be recovered and reused if desired, preferably in a further reaction according to process step e) of the process of the invention. The extractant used, preferably toluene, which is dissolved in the recovered methanesulfonic acid after the extraction to be carried out in this preferred embodiment can be separated off by distillation in order to avoid secondary reactions with 1,1,1-trifluoroacetone and toluene.

The process of the invention therefore comprises, in a further optional process step f), the separation of the target compound of the formula (I) from the reaction mixture obtained in process step e). The desired target compound is usually obtained in a purity of 95% by weight or above, preferably in a purity of 97% by weight or above.

The process of the invention therefore offers an effective route to the desired target compounds of the formula (I), in particular the compounds of the formulae (Ia) and (Ib), which are preferred target compounds for the purposes of the present invention. The process of the invention makes it possible to prepare the abovementioned compounds in a high total yield and high purity.

In a further aspect, the present invention provides a process for preparing 2,6-diphenylphenol of the formula (III)

(III)

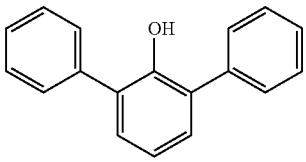

which comprises the steps i) reaction of cyclohexanone in the presence of a basic catalyst to form a reaction mixture comprising the tricyclic condensation products of the formula (IIa), (IIb) and/or (IIc)

(IIa)

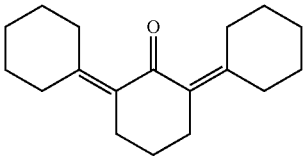

(IIb)

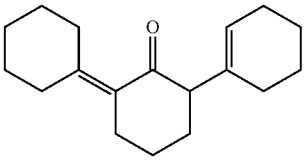

(IIc)

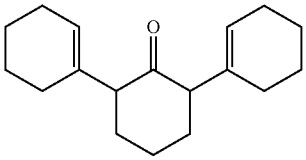

and water in the presence of a solvent or solvent mixture other than cyclohexanone which forms an azeotrope with water, with the water formed being separated off from the reaction mixture by distillation in the form of an azeotrope with the solvent used during the reaction, ii) separation of a mixture of the tricyclic condensation products comprising the compounds of the formulae (IIa), (IIb) and/or (IIc) from the reaction mixture formed in step i) and iii) dehydrogenation of the tricyclic condensation products comprising the compounds of the formulae (IIa), (IIb) and/or (IIc) obtained in step ii) in the presence of a supported transition metal catalyst in the condensed phase to form a reaction mixture comprising 2,6-diphenylphenol of the formula (III)

(III)

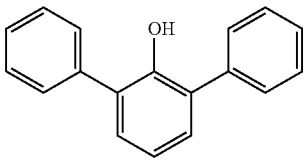

This aspect of the present invention accordingly concerns a process for preparing 2,6-diphenylphenol which corresponds to process steps a) to c) of the above-described process, with the self-condensation of cyclohexanone being carried out in the presence of a basic catalyst according to process step i) in the presence of a solvent or solvent mixture which forms an azeotrope with water (and is different from cyclohexanone) and the water formed being separated off from the reaction mixture by distillation in the form of an azeotrope with the solvent used during the reaction.

The term "solvent which forms an azeotrope with water" can have the same general and preferred meanings as described above under process step a). Accordingly, the term "solvents which form an azeotrope with water" as used for the purposes of this aspect of the present invention, too, refers to preferably organic solvents which are inert under the reaction conditions and have a boiling point at atmospheric pressure of from about 100° C. to about 200° C., preferably in the range from 100 to 150° C., particularly preferably in the range from 110 to 140° C. and very particularly preferably in the range from 130 to 140° C., and are different from cyclohexanone. Particular preference is given to those organic solvents which together with water form an azeotrope which has a boiling point lower than that of cyclohexanone, i.e. lower than 155° C., and a boiling point lower than the respective solvent itself (low-boiling azeotrope). Among these, very particular preference is given to solvents or solvent mixtures whose azeotropic boiling point is below the azeotropic boiling point of cyclohexanone of 95° C. To ensure a satisfactory reaction rate, it is advantageous for the azeotropic boiling point of the solvent or solvent mixture selected to be as high as possible, preferably 70° C. or above, particularly preferably 80° C. or above. Solvents which are particularly preferably used according to the invention in process step a) of the process of the invention accordingly have an azeotropic boiling point in the range from 70° C. to 95° C., preferably from 80° C. to 95° C., particularly preferably up to <95° C., for example toluene, xylene and ethylbenzene or mixtures thereof, preferably xylene. The "solvent which forms an azeotrope with water" mentioned can therefore also be referred to as an entrainer.

The solvents mentioned can be used as such or in the form of mixtures of two or more different solvents. Preference is given to using only one solvent, preferably one which together with water forms an azeotrope as described above, in process step i) of the process of the invention.

According to this aspect of the present invention, process step i) of the process of the invention is carried out so that the water formed by aldol self-condensation of cyclohexanone is separated off from the reaction mixture by distillation in the form of an azeotrope with the solvent used during the reaction. The removal of the water of reaction formed in the aldol self-condensation of cyclohexanone and, if appropriate, the water added in the form of an aqueous solution of the basic catalyst can be effected by the azeotropic distillation methods known per se to those skilled in the art using likewise known apparatuses for separating off or removing water from a reaction mixture, for example a water separator. The water can be removed completely or largely completely or only partly. However, preference is given to separating off the stoichiometrically expected amount of water to be formed (and any amount of water added with the catalyst) to a very substantial extent in order to aid the desired formation of the tricyclic reaction products mentioned.

The amount of the solvent which forms an azeotrope with water to be used according to this aspect of the present invention can be selected within a wide range and can depend on various factors, in particular on the choice of the particular solvent or solvent mixture used and on the process or the apparatus used for separating off or removing the water. The solvent selected is usually, taking into account economic factors, used in an amount, based on the amount of cyclohexanone used, of from 5 to 100% by weight, preferably from 10 to 60% by weight and particularly preferably from 15 to 40% by weight.

As regards the basic catalysts to be used in process step i) and further features of this process step, reference is made to the entirety of the above description of process step a) including all preferred embodiments and their combinations.

Accordingly, the reaction in process step i) is generally carried out in the presence of a basic catalyst, preferably in the presence of an inorganic, in particular strongly basic catalyst. As basic or strongly basic, in particular inorganic catalysts or bases, mention may be made of those which are able to convert cyclohexanone at least partly into the corresponding enolate anion by deprotonation. The reaction in process step i) is preferably carried out in the presence of a strong base, particularly preferably a base which has a pKb of less than 4. As preferred strong bases for this purpose, mention may be made of the hydroxides, alkoxides, hydrides, amides or carbonates of alkali metals or alkaline earth metals, for example lithium, sodium, potassium, calcium and barium hydroxide, sodium ethoxide, sodium methoxide, potassium tert-butoxide, sodium and potassium hydride, lithium diisopropylamide and also lithium, sodium, potassium, calcium and barium carbonate. Particularly preferred strong bases are the hydroxides and carbonates of the alkali metals or alkaline earth metals, very particularly preferably the hydroxides of the alkali metals. The compounds mentioned can be used in pure form or in the form of mixtures with one another or in the form of mixtures with other bases. They can be used in solid or dissolved form, preferably in the form of aqueous solutions.

In process step i) of the process of the invention, too, preference is given to using an aqueous solution of an alkali metal or alkaline earth metal hydroxide, particularly preferably an aqueous solution of sodium hydroxide, as basic catalyst. If the base selected is used in the form of a solution, preferably in the form of an aqueous solution, the preferred concentration range of the solutions is from about 5 to about 50% by weight (based on the finished solution), particularly preferably from about 25 to about 50% by weight.

Process steps ii) and iii) of the process for preparing 2,6-diphenylphenol described under this aspect of the present invention also correspond to process steps b) and c) of the above-described process for preparing 4,4'-[(1-trifluoromethyl)alkylidene]bis(2,6-diphenylphenols) of the formula (I). The separation to be carried out according to step ii) of a mixture of the tricyclic condensation products comprising the compounds of the formulae (IIa), (IIb) and/or (IIc) from the reaction mixture formed in step i) and the dehydrogenation to be carried out according to step iii) of the tricyclic condensation products comprising the compounds of the formulae (IIa), (IIb) and/or (IIc) obtained in step ii) in the presence of a supported transition metal catalyst in the condensed phase to form a 2,6-diphenylphenol of the formula (III) can accordingly be carried out as described above for process steps b) and c), including all preferred embodiments and their combinations. Accordingly, process step iii) can also be carried out as described above in the presence of a supported transition metal catalyst. Here, suitable supported transition metal catalysts are in principle all those which are known to those skilled in the art as catalysts for such dehydrogenation reactions to form aromatic systems, for example those comprising one or more of the transition metals palladium, platinum, nickel, ruthenium, rhodium on a suitable support. The dehydrogenation in process step iii) is preferably carried out in the presence of a catalyst comprising palladium (Pd) and/or platinum (Pt) on a support. The catalysts which are preferably to be used in process step c) can comprise the transition metals palladium and platinum, in each case either individually or in the form of a mixture with one another, optionally together with further metals. Preference is given to using catalysts which comprise palladium as catalytically active metal. The metals mentioned are used in supported form, i.e. in a form in which they have been applied to materials which are known per se to those skilled in the art as support materials. As suitable support materials, mention may be made by way of example of: silica gel ($SiO_2$), aluminum oxide ($Al_2O_3$), carbon, activated carbon, zirconium oxide ($ZrO_2$), titanium dioxide ($TiO_2$). In a preferred embodiment, the dehydrogenation in process step iii) of the process of the invention is carried out in the presence of a Pd catalyst supported on $Al_2O_3$ or on a carbon support such as activated carbon. Here, the $Al_2O_3$ can be used in the form of $\gamma$-$Al_2O_3$ (gamma-$Al_2O_3$) or in the form of $\delta$-$Al_2O_3$ (delta-$Al_2O_3$) or in the form of $\theta$-$Al_2O_3$ (theta-$Al_2O_3$) or in the form of $\delta/\theta$-$Al_2O_3$ (delta/theta-$Al_2O_3$) or in the form of $\alpha$-$Al_2O_3$ (alpha-$Al_2O_3$). Preference is given to using $\gamma$-$Al_2O_3$ (gamma-$Al_2O_3$) as support. A supported catalyst which is particularly preferred for the purposes of the present invention is therefore Pd on $\gamma$-$Al_2O_3$ (gamma-$Al_2O_3$).

The catalytically active metals, preferably palladium and/or platinum, are usually present in the supported catalyst in a proportion by weight of from about 0.1 to about 20% by weight, preferably from about 0.1 to 10% by weight (in each case based on the finished catalyst). They are usually used, depending on the type of catalyst used, in an amount of from 1 to 40% by weight, preferably from 1 to 35% by weight, based on the weight of the mixture of tricyclic ketones to be dehydrogenated.

In a further preferred embodiment, the dehydrogenation in process step iii) can, in addition to the supported transition metal catalyst used, be carried out in the presence of hydroxides or carbonates of alkali metals or alkaline earth metals, for example in the presence of lithium, sodium, potassium, calcium or barium hydroxide and/or lithium, sodium, potassium, calcium or barium carbonate. The basic compounds mentioned can, depending on the type of compound or compounds used, be used in an amount of usually from 3 to 20% by weight, based on the supported catalyst used. As an alternative, supports or supported catalysts pretreated with alkali metal or alkaline earth metal hydroxides or carbonates as mentioned above can also be used.

Here, the catalyst recovered in each case can in principle be used for so long and as often as it still has the desired activity. This generally depends on the catalyst selected in each case, on the starting materials selected and on the reaction conditions. When a catalyst comprising palladium (Pd) and/or platinum (Pt), especially palladium (Pd), on a support is used, this can usually be recirculated, i.e. reused, up to about ten or more times, but at least up to five times or up to four times, without appreciable decreases in activity or selectivity occurring in the dehydrogenation reaction.

The above-described addition of hydroxides or carbonates of alkali metals or alkaline earth metals in process step iii), which is preferred according to the invention, can also have an advantageous effect on the activity, operating life or reusability of the supported transition metal catalyst used in each case. The addition of alkali metal or alkaline earth metal carbonates, preferably sodium and/or potassium carbonate and very particularly preferably potassium carbonate ($K_2CO_3$), in particular, can lead to an increase in activity and thus to improved reusability of the supported catalyst used in each case. This effect is particularly pronounced in reactions using supported palladium catalysts, especially in reactions using the particularly preferred Pd on $\gamma$-$Al_2O_3$ (gamma-$Al_2O_3$) as catalyst. In a particularly preferred embodiment, step iii) of the process of the invention is accordingly carried out in the presence of Pd on $\gamma$-$Al_2O_3$ (gamma-$Al_2O_3$) as supported transition metal catalyst and in the presence of an alkali metal carbonate, preferably in the presence of potassium carbonate.

If desired, an additional process step iv) involving the separation of 2,6-diphenylphenol of the formula (III) from the reaction mixture formed in step iii) can be carried out after process step iii). This additional process step iv) corresponds to process step d) of the above-described process for preparing the compounds of the formula (I) and can accordingly be carried out as described above for process step d), including all preferred embodiments and their combinations.

The following examples illustrate the invention without restricting it in any way:

Gas-chromatographic analyses were carried out by the following method:

30 m RTX 200, ID. 0.25 mm, FD: 0.50 μm; 200° C., 3° C./min-290° C.; $t_R$ (min) $t_R$ (bicyclic ketones of the formulae (Va, Vb)): 8.4, 8.8; $t_R$ (tricyclic ketones of the formulae (IIa, IIb, IIc)): 17.1, 18.2, 18.5; $t_R$ (2-cyclohexyl-6-phenylphenol): 15.2; $t_R$ (2,6-diphenylphenol): 18.7; $t_R$ ($\alpha$-phenyldibenzofuran): 21.6. Concentrations of the crude products obtained (% by weight) were determined by GC analysis using an internal standard.

HPLC analyses were carried out by the following method: CC250/4 Nucleodur C18 Gravity, 5 μm; C: water-0.05% $H_3PO_4$; D: acetonitrile 20:80; outlet: 93 bar, 25° C.; $t_R$ (min) $t_R$ (2,6-diphenylphenol): 4.8; $t_R$ (4,4'-[1-(trifluoromethyl) ethylidene]bis(2,6-diphenylphenol)): 14.5.

EXAMPLE 1

Self-Condensation of Cyclohexanone 900 g (9.1 mol) of cyclohexanone together with 190 g of xylene were placed in a flask at room temperature. 33 g (0.21 mol) of NaOH solution (25%) were subsequently added. The reaction solution was stirred under reflux. Over a period of 7 hours, the temperature of the reaction mixture rose from 120 to 180° C., with 126 ml of water being removed by means of a water separator. The reaction solution was subsequently cooled to room temperature.

To work up the reaction solution, 500 g of water were added to this solution and the solution was neutralized with 11 g of $H_3PO_4$ (85%). The phases were separated at 90° C. The organic phase was subsequently washed at 90° C. with 500 g of $NaHCO_3$ solution (2%). Phase separation was likewise carried out at 90° C.

This gave 965 g of a crude product having the following composition: tricyclic ketones (formulae (IIa, IIb, IIc)): 48.3%; bicyclic ketones (formulae (Va, Vb)): 24.6% (in each case in GC-% by weight).

The crude product (965 g) was distilled batchwise in a laboratory glass column provided with 1 m of Sulzer DX packing (number of theoretical plates: about 20) and having an internal diameter of 50 mm and provided with a still pot and a thin film evaporator with pumped circulation (0.1 $m^2$). The bicyclic ketones (formulae (Va, Vb)) were distilled off at 20 mbar and a temperature at the top of 144° C. from the tricyclic ketones (formulae (IIa, IIb, IIc)) (temperature at the top: 212° C.; 20 mbar). The yield of bicyclic ketones of the formulae (Va, Vb) was 223 g (27%) and that of tricyclic ketones of the formulae (IIa, IIb, IIc) was 410 g (50% of theory; 96 GC-% by weight).

EXAMPLE 2

Recirculation of Bicyclic Ketones of the Formulae (Va, Vb)

360 g (3.0 mol) of cyclohexanone and 300 g (1.67 mol) of bicyclic ketones of the formulae (Va, Vb) together with 140 g of xylene were placed in a flask at room temperature. 22.4 g (0.14 mol) of NaOH solution (25%) were subsequently added. The reaction solution was stirred under reflux. Over a period of 5 hours, the temperature rose from 120 to 180° C., with 62 ml of water being removed by means of a water separator. The red reaction solution was cooled to room temperature and a work-up as described in example 1 was carried out.

This gave 728 g of a crude product having the following composition: tricyclic ketones (formulae (IIa, IIb, IIc): 45.7%; bicyclic ketones (formulae (Va, Vb)): 27.0%; xylene: 14.5%; cyclohexanone: 3% (in each case in GC-% by weight).

EXAMPLES 3 to 5

Dehydrogenation of the Tricyclic Ketones of the Formulae (IIa, IIb, IIc) to Form 2,6-diphenylphenol of the Formula (III)

EXAMPLE 3

10 g of Pd/$Al_2O_3$ catalyst (0.5% by weight of palladium on a $\theta$-$Al_2O_3$ (theta-$Al_2O_3$) support in the form of spheres having a diameter of 3 mm) together with 30 g (0.11 mol) of the tricyclic ketones of the formulae (IIa, IIb, IIc) (97%) and 0.3 g of NaOH were placed in a flask at room temperature. The suspension was stirred at 290-300° C. for 4 hours. After the reaction mixture had cooled to room temperature, the reaction mixture was admixed with 200 ml of heptane. The reaction solution was heated to 90° C. and the catalyst was subsequently filtered off and washed with 100 ml of heptane. The crude product was evaporated on a rotary evaporator.

This gave a crude product having the following composition: 2,6-diphenylphenol: 71.3%, tricyclic ketones of the formulae (IIa, IIb, IIc): 8.2% (in each case in GC-% by weight) and 2-cyclohexyl-6-phenylphenol: 5.0 GC-% by area. The 2,6-diphenylphenol product was isolated by crystallization from heptane (120 ml) in a yield of 62% (17.8 g, 97 GC-% by weight).

EXAMPLE 4

10 g of Pd/$Al_2O_3$ (0.72% by weight of palladium on a $\gamma$-$Al_2O_3$ (gamma-$Al_2O_3$) support in the form of extrudates having a length of 4 mm) together with 30 g (0.11 mol) of the tricyclic ketones of the formulae (IIa, IIb, IIc) (97%) and 0.3 g of NaOH were placed in a flask at room temperature. The suspension was stirred at 290-300° C. for 8 hours. The reaction mixture was cooled to 95° C., admixed with 200 ml of heptane and a work-up as described in example 3 was carried out.

This gave a crude product having the following composition: 2,6-diphenylphenol: 44.8%, tricyclic ketones of the formulae (IIa, IIb, IIc): 4.9% (in each case in GC-% by weight) and 2-cyclohexyl-6-phenylphenol: 12.3 GC-% by area.

The 2,6-diphenylphenol product was isolated by crystallization from heptane in a yield of 34% (9.5 g, 99 GC-% by area).

EXAMPLE 5

10 g of $Pd/Al_2O_3$ (0.72% by weight of palladium on a $\gamma$-$Al_2O_3$ (gamma-$Al_2O_3$) support in the form of extrudates having a length of 4 mm) together with 30 g (0.11 mol) of the tricyclic ketones of the formulae (IIa, IIb, IIc) (97%) and 1.5 g of $K_2CO_3$ were placed in a flask at room temperature. The suspension was stirred at 290-300° C. for 8 hours. The reaction mixture was cooled to 90° C., admixed with 200 ml of heptane and a work-up as described in example 3 was carried out.

This gave a crude product having the following composition: 2,6-diphenylphenol: 47.3%, tricyclic ketones of the formulae (IIa, IIb, IIc): 5.8% (in each case in GC-% by weight) and $\alpha$-phenyldibenzofuran: 13.6 GC-% by area. The 2,6-diphenylphenol product was isolated by crystallization from heptane in a yield of 44% (12.5 g, 99 GC-% by area).

EXAMPLE 6

10 g of $Pd/Al_2O_3$ catalyst (0.72% by weight of palladium on a $\gamma$-$Al_2O_3$ (gamma-$Al_2O_3$) support in the form of extrudates having a length of 4 mm) together with 30 g (0.12 mol) of the tricyclic ketones of the formulae (IIa, IIb, IIc) (97%) were placed in a flask at room temperature. The suspension was stirred at 290-300° C. for 8 hours. This gave a crude product having the following composition: 2,6-diphenylphenol: 25.7%, tricyclic ketones of the formulae (IIa, IIb, IIc): 10.3% (in each case in GC-% by weight) and 2-cyclohexyl-6-phenylphenol: 34.6 GC-% by area.

EXAMPLE 7

0.24 g of 5% Pd/C catalyst and 15 g (0.06 mol) of the tricyclic ketones of the formulae (IIa, IIb, IIc) (97%) were placed in a flask at room temperature. The suspension was stirred at 290-300° C. for 2 hours. The suspension was cooled and, at 25° C., diluted with 50 ml of acetone. The catalyst was filtered off and the crude product was evaporated on a rotary evaporator. The 2,6-diphenylphenol product was subsequently isolated by two-stage crystallization of the crude product (13 g) from heptane/isopropanoll (25:1) in a yield of 50% (7 g, 99 GC-% by area).

EXAMPLE 8

13.3 g of $Pd/Al_2O_3$ (from example 5) together with 30 g (0.11 mol) of the tricyclic ketones of the formulae (IIa, IIb, IIc) (97%) were placed in a flask at room temperature. The suspension was stirred at 295° C. for 8 hours. The reaction mixture was cooled to 60° C. and then admixed with 200 ml of heptane and a work-up as described in example 3 was carried out. The catalyst which had been separated off was reused for the next dehydrogenation reaction.

This gave a crude product (24.5 g) having the following composition: 2,6-diphenylphenol: 54.3%, tricyclic ketones of the formulae (IIa, IIb, IIc): 8.2% (in each case in GC-% by weight) and 2-cyclohexyl-6-phenylphenol: 6.9 GC-% by area and $\alpha$-phenyldibenzofuran: 6.3 GC-% by area.

EXAMPLE 9

Synthesis of 4,4'-[1-(trifluoromethyl)ethylidene]bis(2,6-diphenylphenol)

61.5 g (0.25 mol) of 2,6-diphenylphenol and 875 g of methanesulfonic acid (100%) were placed in a flask. 15.4 g (0.14 mol) of 1,1,1-trifluoroacetone were subsequently added at 20° C. To complete the reaction, the suspension was stirred at 45° C. for 10 hours. The suspension was subsequently cooled to 20° C. and filtered. The filtercake was washed with distilled water (730 g each time) until neutral and dried. This gave 71 g (97% of theory) of 4,4'-[1-(trifluoromethyl)ethylidene]bis(2,6-diphenylphenol) in the form of a white powder (HPLC-% by weight: 98%).

EXAMPLE 10

325 g (1.31 mol) of 2,6-diphenylphenol (99%) and 2400 g of methanesulfonic acid (100%) were placed in a double-walled reactor at 20° C. The suspension was admixed with 81.3 g (0.73 mol) of 1,1,1-trifluoroacetone and stirred at 50° C. for 10 hours. After the reaction was complete, the suspension was admixed with 4200 g of toluene and the reaction mixture was stirred at 50° C. for 30 minutes. The phases were separated at 50° C. and the toluene phase was washed with 1680 g of water, 1680 g of 2% strength sodium carbonate solution and 1680 g of water. The solvent toluene was distilled off. This gave 376 g (95% of theory) of 4,4'-[1-(trifluoromethyl)ethylidene]bis(2,6-diphenylphenol) in the form of a white powder (HPLC-% by weight: 97%).

The invention claimed is:

1. A process for preparing 4,4'-[1-(trifluoromethyl)alkylidene]bis(2,6-diphenylphenols) of the formula (I)

(I)

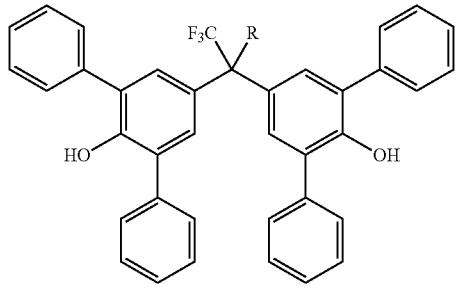

where the radical

R is unbranched or branched $C_1$-$C_6$-alkyl or $C_1$-$C_6$-perfluoroalkyl, which comprises the process steps a) reaction of cyclohexanone in the presence of a basic catalyst to form a reaction mixture comprising the tricyclic condensation products of the formula (IIa), (IIb) and/or (IIc)

(IIa)

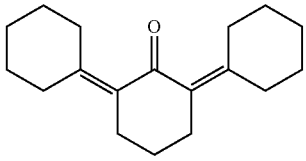

-continued (IIb)

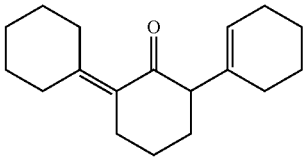

(IIc)

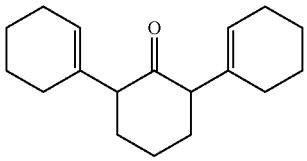

and water, b) separation of a mixture of the tricyclic condensation products comprising the compounds of the formulae (IIa), (IIb) and/or (IIc) from the reaction mixture formed in step a), c) dehydrogenation of the tricyclic condensation products comprising the compounds of the formulae (IIa), (IIb) and/or (IIc) obtained in step b) in the presence of a $Al_2O_3$ supported [transition metal] *Pd* catalyst, *and carbonates of alkali metals or alkaline earth metals,* in the condensed phase to form a reaction mixture comprising 2,6-diphenylphenol of the formula (III), (III)

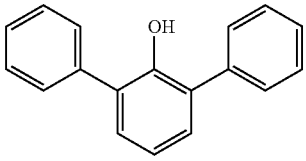

d) separation of 2,6-diphenylphenol of the formula (III) from the reaction mixture formed in step c) and e) reaction of the 2,6-diphenylphenol of the formula (III) obtained in step d) with a trifluoromethyl ketone of the formula (IV)

(IV)

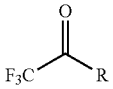

where the radical R is as defined for formula (I), in the presence of a strong organic acid to form the 4,4'-[1-(trifluoromethyl)alkylidene]bis(2,6-diphenylphenol) of the formula (I).

2. The process of claim 1, wherein an aqueous solution of an alkali metal hydroxide or alkaline earth metal hydroxide is used as basic catalyst in step a).

3. The process of claim 1, wherein an aqueous solution of sodium hydroxide is used as basic catalyst in step a).

4. The process of claim 1, wherein the reaction according to step a) is carried out at a temperature in the range from 90 to 180° C.

5. The process of claim 1, wherein the reaction according to process step a) is carried out in the presence of a solvent or solvent mixture which forms an azeotrope with water.

6. The process of claim 5, wherein the water formed in step a) is separated from the reaction mixture by distillation in the form of an azeotrope with the solvent or solvent mixture used during the reaction.

7. The process of claim 5, wherein xylene, toluene or ethylbenzene or a mixture thereof is used as solvent.

8. The process of claim 1, wherein the separation according to process step b) is carried out in the form of a distillation.

[9. The process of claim 1, wherein the dehydrogenation according to process step c) is carried out in the presence of a catalyst comprising palladium and/or platinum on a support.]

[10. The process of claim 1, wherein the dehydrogenation according to process step c) is carried out in the presence of a Pd catalyst supported on $Al_2O_3$ or a carbon support.]

[11. The process of claim 1, wherein the dehydrogenation according to process step c) is carried out in the presence of hydroxides or carbonates of alkali metals or alkaline earth metals.]

12. The process of claim 1, wherein the isolation of 2,6-diphenylphenol according to process step d) is carried out in the form of a crystallization.

13. The process of claim 1, wherein the reaction according to process step e) is carried out at a temperature in the range from 10 to 60° C.

14. The process of claim 1, wherein the reaction according to process step e) is carried out in the presence of an organic acid having a pKa of up to 2.

15. The process of claim 1, wherein the reaction according to process step e) is carried out in the presence of methanesulfonic acid.

16. The process of claim 1, wherein 2,6-diphenylphenol and the trifluoromethyl ketone of the formula (IV) are used in a molar ratio of from 1:1 to 2:1 in process step e).

17. The process of claim 1, wherein the radical R is methyl or trifluoromethyl.

18. The process of claim 1, wherein the radical R is methyl.

19. The process of claim 1, wherein the 4,4'-[1-(trifluoromethyl)alkylidene]bis(2,6-diphenylphenol) of the formula (I) formed in process step e) is separated off from the resulting reaction mixture by extraction.

20. A process for preparing 2,6-diphenylphenol of the formula (III)

(III)

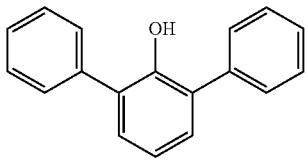

which comprises the steps i) reaction of cyclohexanone in the presence of a basic catalyst to form a reaction mixture comprising the tricyclic condensation products of the formula (IIa), (IIb) and/or (IIc)

(IIa)

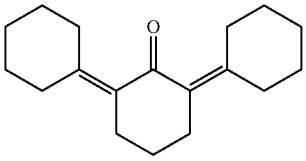

(IIb)

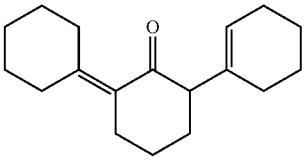

(IIc)

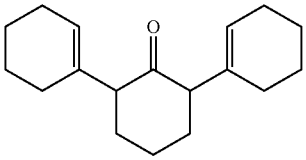

and water in the presence of a solvent or solvent mixture other than cyclohexanone which forms an azeotrope with water, with the water formed being separated off from the reaction mixture by distillation in the form of an azeotrope with the solvent or solvent mixture used during the reaction, ii) separation of a mixture of the tricyclic condensation products of the formulae (IIa), (IIb) and/or (IIc) from the reaction mixture formed in step i) and iii) dehydrogenation of the tricyclic condensation products comprising the compounds of the formulae (IIa), (IIb) and/or (IIc) obtained in step ii) in the presence of a $Al_2O_3$ supported [transition metal] *Pd* catalyst, *and carbonates of alkali metals or alkaline earth metals,* in the condensed phase to form a reaction mixture comprising 2,6-diphenylphenol of the formula (III)

(III)

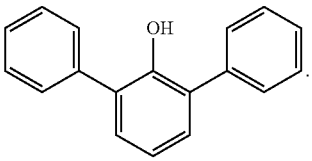

*21. A process for dehydrogenating compounds of formula (IIa), (IIb), and/or (IIc)*

(IIa)

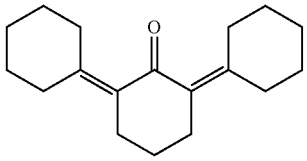

(IIb)

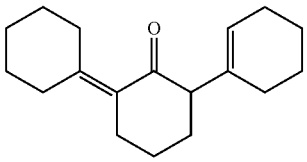

(IIc)

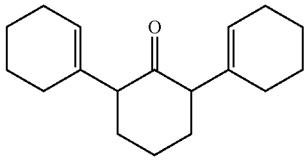

*in the presence of an $Al_2O_3$ supported Pd catalyst, and carbonates of alkali metals, in the condensed phase to form a reaction mixture comprising 2,6-diphenylphenol of formula (III),*

(III)

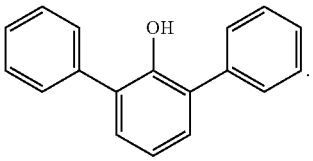

*22. The process of claim 21, further comprising separating the supported Pd catalyst from the reaction mixture and reuse the catalyst for at least four times in subsequent dehydrogenation processes of compounds of formula (IIa), (IIb), and/or (IIc) without appreciable decreases in activity or selectivity.*

*23. The process of claim 1, further comprising separating the supported Pd catalyst from the reaction mixture and reuse the catalyst for at least four times in subsequent dehydrogenation processes of compounds of formula (IIa), (IIb), and/or (IIc) without appreciable decreases in activity or selectivity.*

*24. The process of claim 20, further comprising separating the supported Pd catalyst from the reaction mixture and reuse the catalyst for at least four times in subsequent dehydrogenation processes of compounds of formula (IIa), (IIb), and/or (IIc) without appreciable decreases in activity or selectivity.*

* * * * *